(12) United States Patent
Binggeli et al.

(10) Patent No.: US 6,586,422 B2
(45) Date of Patent: Jul. 1, 2003

(54) PYRAZINE AND TRIAZINE DERIVATIVES OF 1,2,4,5-TETRAHYDRO-BENZO OR THIENO [D] AZEPINE

(75) Inventors: Alfred Binggeli, Benningen (CH); Hans-Peter Maerki, Basel (CH); Vincent Mutel, Mulhouse (FR); Maurice Wilhelm, Morschwiller le Bas (FR); Wolfgang Wostl, Grenzach-Whylen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/020,680

(22) Filed: Dec. 12, 2001

(65) Prior Publication Data

US 2002/0123488 A1 Sep. 5, 2002

(30) Foreign Application Priority Data

Dec. 22, 2000 (EP) ............................................. 00128329

(51) Int. Cl.[7] .......................... A61K 31/55; A61P 25/06; A61P 25/04; C07D 223/16
(52) U.S. Cl. .................. 514/215; 514/217.01; 540/593; 540/594
(58) Field of Search ........................... 514/215, 217.01; 540/593, 594

(56) References Cited

U.S. PATENT DOCUMENTS 6,218,385 B1 * 4/2001 Adam et al. ........... 514/217.01

FOREIGN PATENT DOCUMENTS

| EP | 074 549 | 3/1983 |
|----|---------|--------|
| EP | 1 074 549 A2 | 2/2000 |
| EP | 1 059 090 | 12/2000 |
| WO | WO 00/20001 | 4/2000 |
| WO | WO 00/26198 | 5/2000 |

OTHER PUBLICATIONS

Monn et al., Metabotropic Glutamate Receptor Modulators: Recent Advances and Therapeutic Potential, Annual Reports in Medicinal Chemistry, vol. 35, pp. 1–10, 2000.*
Jim J. Huang, *J. Org. Chem.*, vol. 50, pp. 2293–2298 (1985).
A. Brossi et al., *J. Heteroycl. Chem.*, vol. 8(5), pp. 779–783 (1971).
Taylor et al., *J. Org. Chem.*, vol. 37, No. 24, pp. 3958–3960 (1972).
Reuben G.Jones, *J. Amer. Chem. Soc.*, vol. 71, pp. 78–81 (1949).
Fleury et al., *Helvetica Chimica Acta*, vol. 69, pp. 793–802 (1986).
Fleury et al., *Helvetica Chimica Acta*, vol. 73, pp. 1210–1214 (1990).
Taylor et al., *J. Org. Chem.*, Gol. 40, No. 18, pp. 2341–2347 (1975).
Alain Badorc et al., J. Heterocyclic Chem., vol. 22, pp. 1011–1016 (1985).

* cited by examiner

Primary Examiner—Brenda Coleman
(74) Attorney, Agent, or Firm—George W. Johnston; Patricia S. Rocha-Tramaloni; Lyman H. Smith

(57) ABSTRACT

The invention relates to compounds which are represented by the formula

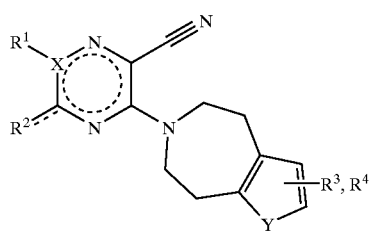

wherein $R^1$, $R^2$, $R^3$, $R^4$, X and Y are as defined in the specification, as well as pharmaceutically acceptable salts thereof. The invention further relates to pharmaceutical compositions containing these compounds and to a process for their preparation. The compounds possess affinity towards metabotropic glutamate receptors and are therefore useful in the treatment or prevention of acute and/or chronic neurological disorders.

24 Claims, No Drawings

PYRAZINE AND TRIAZINE DERIVATIVES OF 1,2,4,5-TETRAHYDRO-BENZO OR THIENO [D] AZEPINE

FIELD OF INVENTION

The present invention relates to compounds with activity as antagonists at metabotropic gluatmate receptors and more particularly to pyrazine and triazine derivatives of 1,2,4,5-tetrahydro-Benzo or Thieno [d]azepine that demonstrate activity as group I mGluR antagonists.

BACKGROUND

In the central nervous system (CNS) the transmission of stimuli takes place by the interaction of a neurotransmitter, which is sent out by a neuron, with a neuroreceptor. L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present, eight different members of these mGluRs are known and of these some even have sub-types. On the basis of structural parameters, the different second messenger signaling pathways and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as epilepsy, stroke, chronic and acute pain, psychosis, schizophrenia, Alzheimer's disease, cognitive disorders and memory deficits. Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by pharmaceutical compositions as well as conditions which lead to glutamate-deficiency functions, such as e.g. muscle spasms, convulsions, migraine, urinary incontinence, nicotine addiction, opiate addiction, anxiety, vomiting, dyskinesia and depression.

SUMMARY

The present invention is a compound of the formula

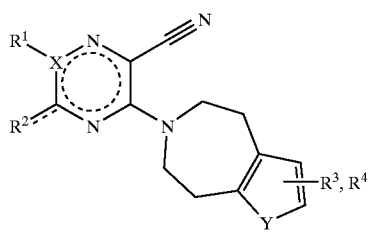

I wherein
$R^1$ is selected from the group consisting of hydrogen, lower alkyl, lower alkenyl, or unsubstituted phenyl or phenyl substituted in meta or para position with at least one substituents selected from the group consisting of lower alkyl, lower alkoxy or halogen, or is absent, in the case when X is —N= or =N—;

$R^2$ is selected from the group consisting of hydrogen, lower alkyl, lower alkenyl, =O, —S-lower alkyl, —SO$_2$-lower alkyl or —OR, —O(CHR$^a$)$_{m+1}$—OR$^b$, NR$^c_2$, NHNR$^d_2$, —N(R$^e$)(CHR$^f$)$_{m+1}$—OR$^g$, —N(R$^h$)(CHR$^i$)$_m$-pyridino, —N(R$^j$)(CHR$^k$)$_n$—(C$_3$-C$_6$)cycloalkyl, —N(R$^l$)(CHR$^m$)$_m$(CR$^n_2$)—NR$^o_2$, or —N(R$^p$)(CHR$^q$)$_{m+1}$—NH—C(O)—O-lower alkyl;

m is 1, 2, 3, 4, 5 or 6;

n is 0, 1, 2, 3, 4 or 5;

R and R$^{a-q}$ are independently selected from the group consisting of hydrogen, lower alkyl or lower alkenyl;

X is selected from the group consisting of —N=, =N—, >C= or =C<; and, in the case where R$^2$ is =O or alkenyl, the dotted line is a bond, Y is selected from the group consisting of —CH=CH—, —CH=CR$^3$—, —CR$^3$=CH—, —CR$^3$—CR$^4$— or s; and R$^3$, R$^4$ are selected, independently from each other, from the group consisting of hydrogen, lower alkyl, lower alkoxy or halogen with the proviso, that when Y represents a vinylene group, only one group R$^3$ and one group R$^4$ are present in the resultant benzene ring;

or a pharmaceutically acceptable salt thereof in racemic and optically active form.

It has surprisingly been found that the compounds of formula I are antagonists at metabotropic glutamate receptors.

Objects of the present invention are compounds of formula I and pharmaceutically acceptable salts thereof and their use as pharmaceutically active substances. Methods for the preparation of the above mentioned substances and pharmaceutical compositions based on compounds in accordance with the invention and their production are also objects of the present invention as well as the use of the compounds in accordance with the invention in the control or prevention of illnesses treated by modulation of metabotropic glutamate receptors, and, respectively, for the production of corresponding pharmaceutical compositions.

DETAILED DESCRIPTION

Preferred compounds of formula I within the scope of the present invention are those having the formula

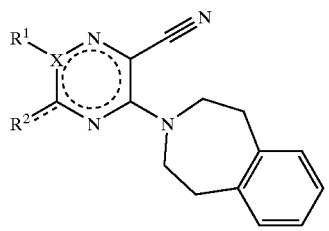

I-A wherein
$R^1$ is selected from the group consisting of hydrogen, lower alkyl, lower alkenyl, or unsubstituted phenyl or phenyl substituted in meta or para positions with at least one substituent selected from the group consisting of lower alkyl, lower alkoxy or halogen, or is absent, when X is —N= or =N—;

$R^2$ is selected from the group consisting of hydrogen, lower alkyl, lower alkenyl, =O, —S-lower alkyl, —SO$_2$-lower alkyl or —OR, —O(CHR$^a$)$_{m+1}$—OR$^b$, —NR$^c_2$, —NH—NR$^d_2$, —N(R$^e$)(CHR$^f$)$_{m+1}$—OR$^g$, —N(R$^h$)(CHR$^i$)$_m$-pyridino, N(R$^j$)(CHR$^k$)$_n$—(C$_3$–C$_6$)cycloalkyl, —N(R$^l$)(CHR$^m$)$_m$(CR$^n_2$)NR$^o_2$, or —N(R$^p$)(CHR$^q$)$_{m+1}$—NH—C(O)—O-lower alkyl;

m is 1, 2, 3, 4, 5 or 6;

n is 0, 1, 2, 3, 4 or 5;

R and R$^{a-q}$ are independently selected from the group consisting of hydrogen, lower alkyl or lower alkenyl;

X is selected from the group consisiting of —N=, =N—, >C= or =C<; the dotted line is a bond when R is =O or lower alkenyl; and a pharmaceutically acceptable salt thereof in racemic and optically active form.

Preferred compounds of formula I-A within the scope of the present invention are those, in which R$^1$ is absent and X is —N= or =N—; and R$^2$ is —NR$^c_2$, —NH—NR$^d_2$, —N(R$^e$)(CHR$^f$)$_{m+1}$—OR$^g$, —N(R$^h$)(CHR$^i$)$_m$-pyridino, —N(R$^j$)(CHR$^k$)$_n$—(C$_3$–C$_6$) cycloalkyl, —N(R$^l$)(CHR$^m$)$_m$(CR$^n_2$)NR$^o_2$, or —N(R$^p$)(CHR$^q$)$_{m+1}$—NH—C(O)—O-lower alkyl.

The following are examples of such compounds:

3-Amino-5-(1,2,4,5-tetrahydro-benzo[d]azepin-3-yl)-[1,2,4]triazine-6-carbonitrile, 3-(cyclopropylmethyl-amino)-5-(1,2,4,5-tetrahydro-benzo[d]azepin-3-yl)-[1,2,4]triazine-6-carbonitrile, 3-(2-hydroxy-ethylamino)-5-(1,2,4,5-tetrahydro-benzo[d]azepin-3-yl)-[1,2,4]triazine-6-carbonitrile, (RS)-3-(2-hydroxy-propylamino)-5-(1,2,4,5-tetrahydro-benzo[d]azepin-3-yl)-[1,2,4]triazine-6-carbonitrile, 3-hydrazino-5-(1,2,4,5-tetrahydro-benzo[d]azepin-3-yl)-[1,2,4]triazine-6-carbonitrile, {2-[6-cyano-5-(1,2,4,5-tetrahydro-benzo[d]azepin-3-yl)-[1,2,4]triazin-3-ylamino]-ethyl}-carbamic acid tert-butyl ester, or 3-(2-pyridin-3-yl-ethylamino)-5-(1,2,4,5-tetrahydro-benzo[d]azepin-3-yl)-[1,2,4]triazine-6-carbonitrile.

Especially preferred are those compounds of formula I-A, in which

R$^1$ is absent and X is —N= or =N—; and

R$^2$ signifies —N(R$^e$)(CHR$^f$)$_{m+1}$—OR$^g$, —N(R$^h$)(CHR$^i$)$^m$-pyridino, or —N(R$^j$)(CHR$^k$)$^n$—(C$_3$–C$_6$)cycloalkyl.

Examples of such compounds are the following:

3-(cyclopropylmethyl-amino)-5-(1,2,4,5-tetrahydro-benzo[d]azepin-3-yl)-[1,2,4]triazine-6-carbonitrile, 3-(2-hydroxy-ethylamino)-5-(1,2,4,5-tetrahydro-benzo[d]azepin-3-yl)-[1,2,4]triazine-6-carbonitrile, (RS)-3-(2-hydroxy-propylamino)-5-(1,2,4,5-tetrahydro-benzo[d]azepin-3-yl)-[1,2,4]triazine-6-carbonitrile, or 3-(2-pyridin-3-yl-ethylamino)-5-(1,2,4,5-tetrahydro-benzo[d]azepin-3-yl)-[1,2,4]triazine-6-carbonitrile.

Compounds of formula I, in which

X signifies >C= or =C< and R$^1$ and R$^2$ are lower alkyl, are also preferred.

The following are examples of such compounds:

5-ethyl-6-methyl-3-(1,2,4,5-tetrahydro-benzo[d]azepin-3-yl)-pyrazine-2-carbonitrile, or 6-ethyl-5-methyl -3-(1,2,4,5-tetrahydro-benzo[d]azepin-3-yl)-pyrazine-2-carbonitrile.

Especially preferred are such compounds of formula I, in which

X signifies >C= or =C< and R$^1$ signifies ethyl.

6-Ethyl-5-methyl-3-(1,2,4,5-tetrahydro-benzo[d]azepin-3-yl)-pyrazine-2-carbonitrile is an example of such a compound.

Also preferred are compounds of formula I, in which

X signifies >C= or =C< and R$^1$ signifies unsubstituted phenyl or phenyl substituted in meta or para positions with one or more substituents selected from the group consisting of lower alkyl, lower alkoxy or halogen.

An example of such a compound is 5-methyl-6-phenyl-3-(1,2,4,5-tetrahydro-benzo[d]azepin-3-yl)-pyrazine-2-carbonitrile.

Further preferred compounds are those, in which

X signifies >C= or =C< and R$^2$ signifies —N(R$^e$)(CHR$^f$)$_{m+1}$—OR$^g$ with R$^{e,f,g}$ signifying independently from each other hydrogen, lower alkyl or lower alkenyl.

5-(2-hydroxy-ethylamino)-3-(1,2,4,5-tetrahydro-benzo[d]azepin-3-yl)-pyrazine-2-carbonitrile is an example of such a compound.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower alkenyl" used in the present description denotes straight-chain or branched unsaturated hydrocarbon residues with 2–7 carbon atoms, preferably with 2–4 carbon atoms.

The term "lower alkoxy" denotes a lower alkyl group as defined above linked to an oxygen group. Preferred alkoxy groups are methoxy or ethoxy.

The term "cycloalkyl" denotes a saturated carbocyclic group containing from 3 to 6 carbon atoms, preferred are cyclopropyl, cyclopentyl or cyclohexyl.

The term "halogen" embraces fluorine, chlorine, bromine and iodine.

The term "phenyl substituted in meta or para position with at least one substituent selected from the group consisting of lower alkyl, lower alkoxy or halogen" means the homocyclic six membered aromatic ring which may be substituted by at least one substituent selected from the group consisting of lower alkyl, lower alkoxy or halogen in the para and/or meta positions, relative to the ring carbon that is attached to one of the carbons of the pyrazine ring of the compounds of formula I.

The compounds of formula I and their pharmaceutically acceptable salts can be manufactured by reacting the compound of the formula

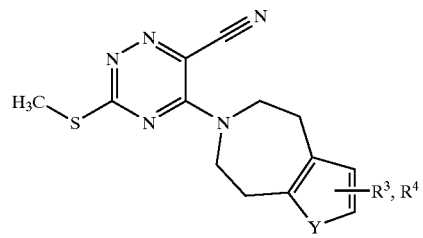

I-2 with nucleophiles to obtain a compound of formula

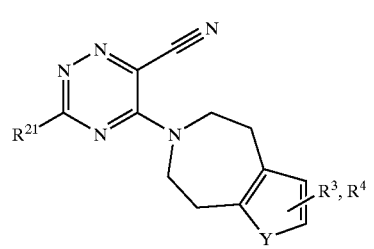

I-1 wherein R²¹ signifies —OR, —O(CHRᵃ)_{m+1}—OR, —NR^c_2, —NH—NR^{dd'}_2, —N(Rᵉ)(CHR^f)_{m+1}—OR^g, —N(R^h)(CHRⁱ)_m-pyridino, —N(R^j)(CHR^k)_n—(C_3-C_6)cycloalkyl, —N(R^l)(CHR^m)_m(CR^n_2)—NR^o_2, or —N(R^p)(CHR^q)_{m+1}—NH—C(O)—O-lower alkyl as defined before, and, if desired, converting a functional group of R²¹ in a compound of formula I-1 into another functional group to obtain another compound of formula I-1, and, if desired, converting a compound of formula I-1 into a pharmaceutically acceptable salt; or reacting a compound of the formula

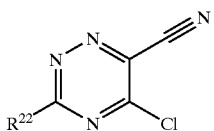

II-1 wherein R²² signifies alkyl, with the compound of formula

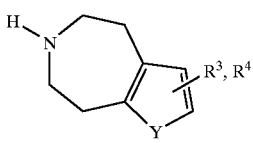

III to obtain a compound of formula

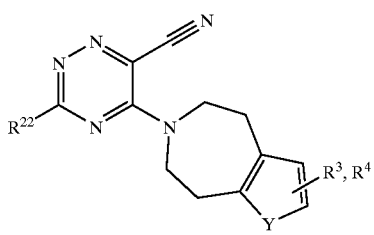

I-3 and, if desired, converting a compound of formula I-3 into a pharmaceutically acceptable salt; or reacting a compound of the formula

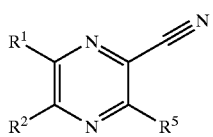

II-2 wherein R⁵ signifies halogen, with the compound of formula

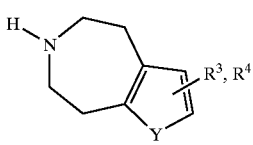

III to obtain a compound of formula

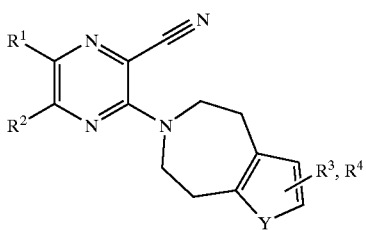

I-4 and, if desired, converting a functional group of R² in a compound of formula 1-4 into another functional group to obtain another compound of formula I-4, and, if desired, converting a compound of formula I-4 into a pharmaceutically acceptable salt.

3-Methylsulfanyl-5-(1,2,4,5-tetrahydro-benzo- or thieno-azepin-3-yl)-[1,2,4]triazine-6-carbonitriles (I-2) are prepared by reaction of 3-(methylthio)-5-chloro-6-cyano-1,2,4-triazine (J. J. Huang, J. Org. Chem. 1985, 50, 2293–2298) with tetrahydro-benzo- or thieno-azepine compounds III, e.g. 2,3,4,5-tetrahydro-1H-benzo[d]azepine hydrochloride (J. Heterocycl. Chem. 1971, 8(5), 779–83), in the presence of a base like triethylamine or ethyl-diisopropylamine in solvents like N,N-dimethylformamide, dimethylsulfoxide, methyl-ethylketone, ethanol, dioxane or tetrahydrofuran at temperatures between 10 and 50° C.

Substitution of the Me—S-group in compound I-2 by optionally substituted N-nucleophiles can be performed in water, ethanol, N,N-dimethylformamide, dimethylsulfoxide, 1,2-dimethoxyethane, preferentially in dioxane at elevated temperatures, preferentially 100° C to 160° C.

Substitution of the Me—S-group in compound I-2 by optionally substituted O-nucleophiles can be performed in an inert solvent as ethers, like 1,2-dimethoxyethane or dioxane at temperatures between room temperature and 120° C. after transformation of the corresponding alcohol into an alcoholate using a base like sodium hydride or potassium hydride.

The functionalization of the O- and N-nucleophiles can also serve as a protective function. Thus, modifications at the other part of the R²¹-substituent are allowed, e.g. removal of a N-protecting group, like the tert-butoxycarbonyl group, by methods well documented in the literature.

Compounds of formula I-1 can also be prepared by oxidation of the thioether I-2 to the corresponding sulfon according to known oxidative methods, e.g. by 3-chloroperbenzoic acid in dichloromethane, followed by treatment with thiolates, alcoholates, amines or aqueous base, e.g. like sodium carbonate or sodium hydrogencarbonate, thus yielding the group R²¹.

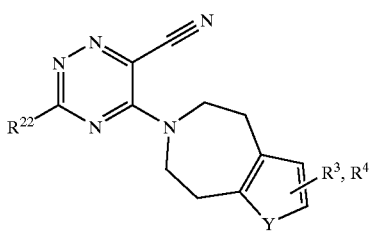

I-3

Compounds of formula I-3 wherein $R^{22}$ signifies lower alkyl can be prepared by reacting the intermediate II-1 with tetrahydro-benzo- or thieno-azepine compounds III, e.g. 2,3,4,5-tetrahydro-1H-benzo[d]azepine hydrochloride (J. Heterocycl. Chem. 1971, 8(5), 779–83), in the presence of a base like triethylamine or ethyl-diisopropylamine in solvents like N,N-dimethylformamide, dimethylsulfoxide, methyl-ethylketone, ethanol, dioxane or tetrahydrofuran at temperatures between 10 and 50° C.

The intermediate II-1 can be synthesized in analogy to the procedure as described in J. Org. Chem. 1972, 37 (24), 3958–3960, starting with the condensation of the corresponding amidrazones IV and methyl or ethyl oxomalonate V, followed by ammonolysis of the ester VI, and, finally, dehydration of the amide VII and substitution of the hydroxy group by chlorine (scheme 1).

with $R^6$ and $R^7$ signifying both independently from each other hydrogen, optionally substituted phenyl, lower alkyl or lower alkenyl, react with 2-amino-malonic acid diamide IX as described in J. Amer. Chem. Soc. 1949,71,78–81, either in the presence of an aqueous base at temperatures between 0° C. and 60° C. or in the absence of a base in solvents like water or an alcohol at temperatures between room temperature and 120° C. to form the two 3-oxo-3,4-dihydro-pyrazine-2-carboxylic acid amides Xa and Xb. Treatment of Xa and Xb either separately or as a mixture with phosphorus oxychloride and optionally additional phosphorus pentachloride in the presence of triethylamine or diethylaniline at temperatures between 40° C. and 120° C. give 3-chloro-pyrazine-2-carbonitriles II-3a and II-3b (scheme 2).

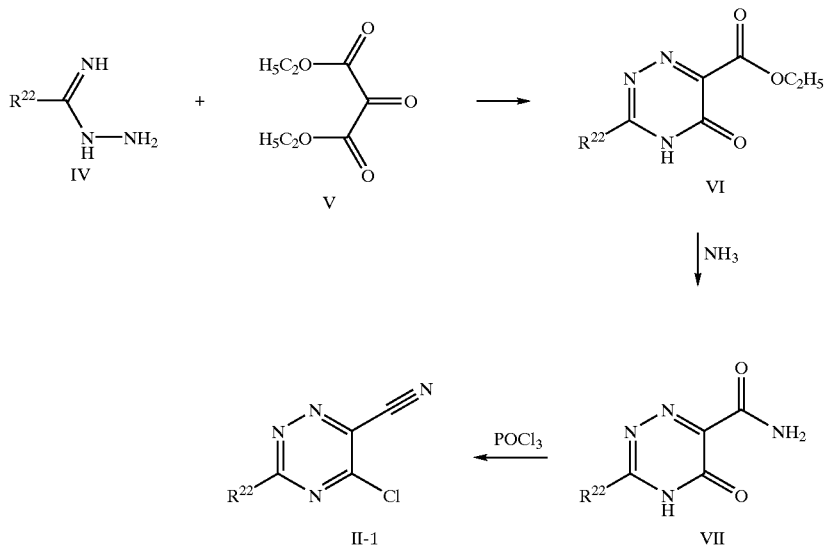

Scheme 1

Compounds of formula

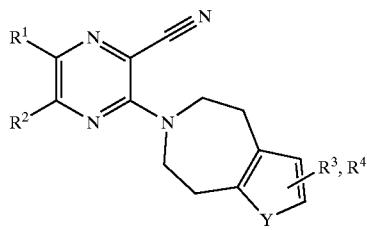

I-4 are prepared by methods as shown in schemes 2, 3 and 4 and described in the following. 1,2-Dicarbonyl compounds VIII

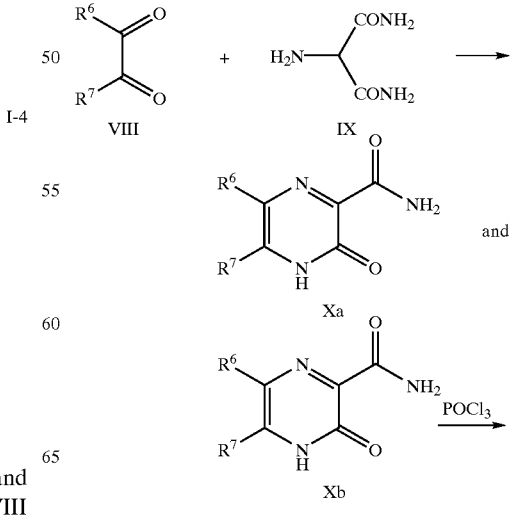

Scheme 2

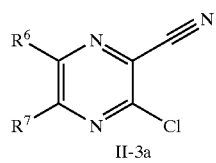

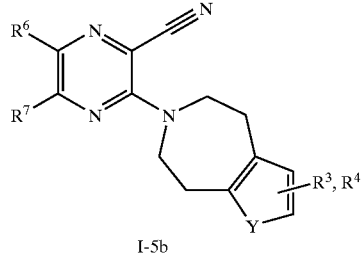

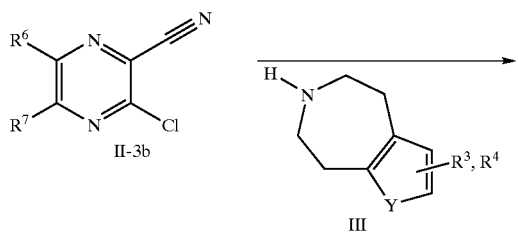

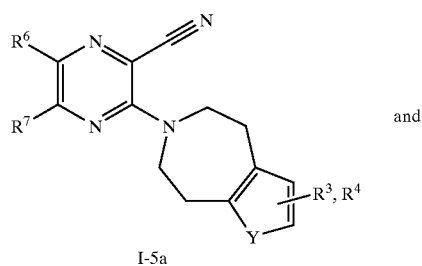

3-Chloro-pyrazine-2-carbonitriles II-3a and II-3b react either separately or as a mixture with tetrahydro-benzo- or thieno-azepine compounds III or their hydrochlorides in solvents like N,N-dimethylformamide, acetonitrile, acetone or dimethylsulfoxide in the presence of a base like potassium carbonate or a tertiary amine as diisopropyl-ethylamine at temperatures between room temperature and 80° C. to form the desired 3-(tetrahydro-benzo- or thieno-azepine-3-yl)-pyrazine-2-carbonitriles I-5a and I-5b, which can be separated by known methods such as chromatography or crystallization.

In an alternative method (scheme 3), bromopyrazine derivatives of formula II-4 are prepared by reacting O-tosylisonitrosomalononitrile XI with morpholino-enamines of formula XII with $R^{11}$ signifying lower alkyl or lower alkenyl, in the presence of a base like pyridine, triethylamine or diisopropyl-ethylamine in aprotic solvents like ether, tetraydrofuran or N,N-dimethylformamide at temperatures between −20° C. and 60° C. to obtain (morpholino-alkenylimino)malononitriles XIII (Helv. Chim. Acta 1986, 69, 793–802). Treatment of the (morpholino-alkenylimino)malononitriles XIII with hydrobromic acid in acetic acid between room temperature and 80° C. induces a cyclisation reaction leading to the bromopyrazines II-4 (Helv. Chim. Acta 1990, 73,1210–1214).

Scheme 3

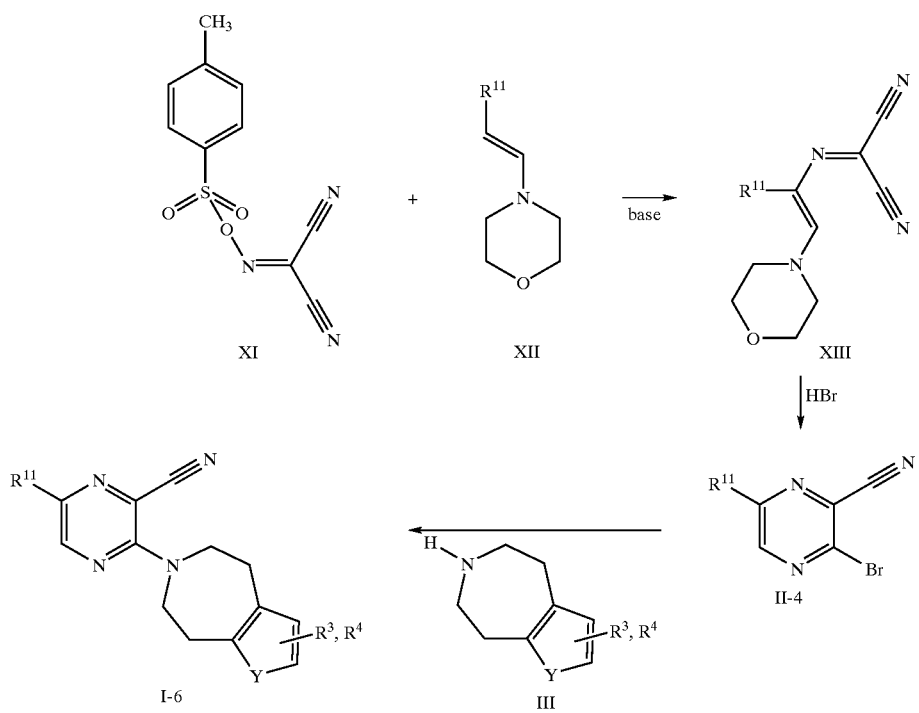

Bromo-pyrazines II-4 react with tetrahydro-benzo or thieno-azepine compounds III or their hydrochlorides in solvents like N,N-dimethylformamide, acetonitrile, acetone or dimethylsulfoxide in the presence of a base like potassium carbonate or a tertiary amine like diisopropyl-ethylamine at temperatures between room temperature and 80° C. to form the desired 3-(tetrahydro-benzo- or thieno-azepine-3-yl)-pyrazine-2-carbonitriles I-6. 3-(Tetrahydro-benzo- or thieno-azepine-3-yl)-pyrazine-2-carbonitriles of formula I-7 can be prepared according to scheme 4.

Diazotization of the 3-amino-5-chloro-2-cyano-pyrazine XIV (J. Org. Chem. 1975, 40, 2341–2347) with t-butyl-nitrite in solvents like acetonitrile or N,N-dimethylformamide in the presence of copper-(II)-bromide at temperatures between room temperature and 95° C. gives the 3-bromo-5-chloro-2-cyano-pyrazine II-5. The 3-bromo-5-chloro-2-cyano-pyrazine II-5 reacts with one equivalent of a primary or secondary amine to two products, in which either the chloro-atom or the bromo-atom is replaced in the amine moiety. If the reaction is performed with a primary amine $R^8NH_2$ in a solvent like dioxane or tetrahydrofuran in the presence of a base like triethylamine or diisopropylethylamine, preferentially at room temperature, then compound II-6 with replaced chloro-atom can be obtained with reasonable selectivity. In a second analogous reaction, tetrahydro-benzo- or thieno-azepine compounds III or their hydrochlorides can then be reacted with II-6 in solvents like N,N-dimethylformamide, tetrahydrofuran, dioxane, acetonitrile, acetone or dimethylsulfoxide and in the presence of a base like potassium carbonate or a tertiary amine like diisopropyl-ethylamine at temperatures between room temperature and 80° C. giving compounds I-7.

Optionally substituted 1,2,4,5-tetrahydro-benzo[d]azepine compounds III

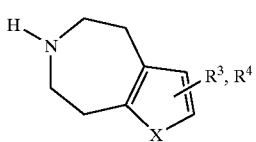

are prepared as described in the Eur. Pat. Appl. EP 1 074 549 A2 (2001). The 5,6,7,8-tetrahydro-4H-thieno[2,3-d]azepine with $R^3$ and $R^4$=H is known (J. Heterocyclic Chem. 1985, 22, 1011). Analogous 5,6,7,8-tetrahydro-4H-thieno[2,3-d]azepine compounds bearing substituents in the thiophene ring can be prepared in close analogy as outlined in scheme 5. Precursor acid chlorides XV bearing preferentially a tosyloxy protective function at the secondary nitrogen atom are cyclized in an inert solvent like 1,2-dichloroethane, dichloromethane or nitrobenzene in the presence of a Lewis acid catalyst like aluminium trichloride, tin tetrachloride or phosphorous pentachloride at temperatures between −40° C. and 80° C. to yield the protected ketones XVI. Hydroxy thieno[2,3-d]azepines XVII can be obtained by simultaneous reduction of the ketone function and removal of the N-tosyl protective function by treatment with sodium bis(methoxyethoxy)aluminium-hydride in toluene at reflux. The hydroxy thieno[2,3-d]azepines XVII can be further reduced to 5,6,7,8-tetrahydro-4H-thieno[2,3-d]azepines XVIII with stannous chloride in acetic acid in the presence of hydrochloric acid at temperatures between room temperature and 100° C.

Scheme 4

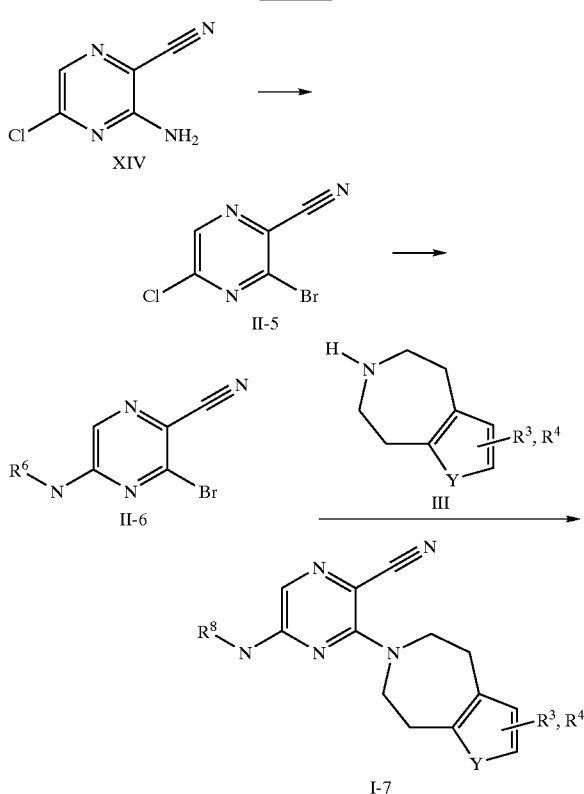

Scheme 5

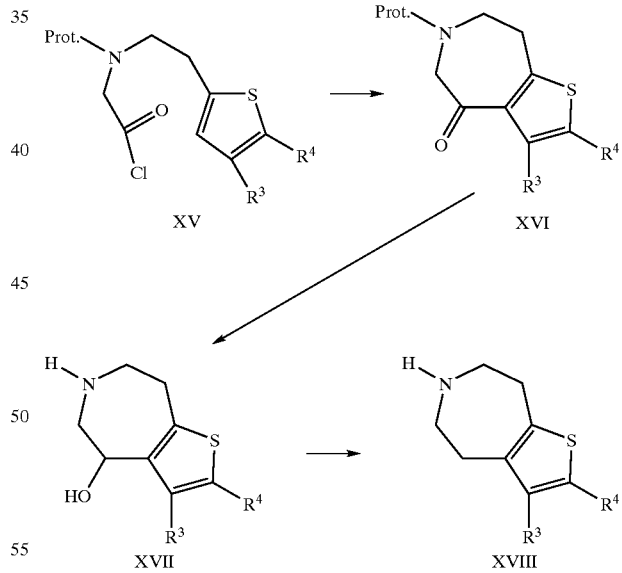

The methods for the preparation of compounds of formula I are described in more detail in examples 1 to 15.

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation or pharmaceutically acceptable salts of acidic compounds of formula I.

The compounds of formula I and their pharmaceutically acceptable salts are, as already mentioned above, metabotropic glutamate receptor antagonists and are therefore useful in the treatment or prevention of diseases which are mediated by metabotropic glutamate receptor antagonists. The compounds of formula I can be used for the treatment or prevention of acute and/or chronic neurological disorders, such as epilepsy, stroke, chronic and acute pain, psychosis, schizophrenia, Alzheimer's disease, cognitive disorders, memory deficits and psychosis. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, ALS, dementia caused by AIDS, eye injuries, retinopathy, idiopathic parkinsonism or parkinsonism caused by pharmaceutical compositions as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression. The compounds are especially useful for the treatment of pain and migraine.

The compounds of the present invention are group I mGluR antagonists. Their pharmacological activity was tested using the following method:

Binding Assay for the Characterization of mGluR 1 Antagonistic Properties

Binding assay with tritiated 1-ethyl-2-methyl-6-oxo-4-(1,1,2-tritritio-1,2,4,5-tetrahydro-benzo[d]azepin-3-yl)-1,6-dihydro-pyrimidine-5-carbonitrile (Eur. Pat. Appl. EP 1 074 549 A2): HEK 293 cells were transiently transfected with the rat mGluR1a receptor. The cells were collected and washed 3 times with PBS. The cell pellets were frozen at −80° C. Membranes were prepared from HEK 293 cells transfected with the rat mGluR1a receptor and used in the binding experiments at 10 μg proteins per assay after resuspension in a HEPES NaOH 20 mM, pH=7.4 binding buffer. 1-Ethyl-2-methyl-6-oxo-4-(1,1,2-tritritio-1,2,4,5-tetrahydro-benzo[d]azepin-3-yl)-1,6-dihydro-pyrimidine-5-carbonitrile (S.A 33.4 Ci/mmol) was used at 3 nM final concentration. The incubation with variable concentrations of potential inhibitors was performed for 1 hour at room temperature, the incubate was then filtered onto GF/B glass fiber filter preincubated 1 hour in PEI 0,1% and washed 3 times with 1 ml of cold binding buffer. The radioactivity retained on the unifilter 96 was counted using a Topcount β counter. After correction for non specific binding the data were normalized and the $IC_{50}$ value calculated using a 4 parameters logistic equation which was fitted to the inhibition curve.

The preferred compounds have an $IC_{50}$ range of 0.001–10.0 μmol/l (B-$IC_{50}$).

In the table below are shown some specific activity data of preferred compounds:

| | Example No. | B-$IC_{50}$ (μM) |
|---|---|---|
| 3-(2-methoxy-ethoxy)-5-(1,2,4,5-tetrahydro-benzo[d]azepin-3-yl)-[1,2,4]triazine-6-carbonitrile | 1 | 3.0 |
| 3-amino-5-(1,2,4,5-tetrahydro-benzo[d]azepin-3-yl)-[1,2,4]triazine-6-carbonitrile | 2 | 0.027 |
| 3-dimethylamino-5-(1,2,4,5-tetrahydro-benzo[d]azepin-3-yl)-[1,2,4]triazine-6-carbonitrile | 3 | 1.38 |
| 3-(cyclopropylmethyl-amino)-5-(1,2,4,5-tetrahydro-benzo[d]azepin-3-yl)-[1,2,4]triazine-6-carbonitrile | 4 | 0.005 |
| 3-(2-hydroxy-ethylamino)-5-(1,2,4,5-tetrahydro-benzo[d]azepin-3-yl)-[1,2,4]triazine-6-carbonitrile | 5 | 0.031 |
| (RS)-3-(2-hydroxy-propylamino)-5-(1,2,4,5-tetrahydro-benzo[d]azepin-3-yl)-[1,2,4]triazine-6-carbonitrile | 6 | 0.027 |
| 3-hydrazino-5-(1,2,4,5-tetrahydro-benzo[d]azepin-3-yl)-[1,2,4]triazine-6-carbonitrile | 7 | 0.37 |
| {2-[6-cyano-5-(1,2,4,5-tetrahydro-benzo[d]azepin-3-yl)-[1,2,4]triazin-3-ylamino]-ethyl}-carbamic acid tert-butyl ester | 8 | 0.027 |
| 3-(2-pyridin-3-yl-ethylamino)-5-(1,2,4,5-tetrahydro-benzo[d]azepin-3-yl)-[1,2,4]triazine-6-carbonitrile | 9 | 0.029 |
| 6-ethyl-5-methyl-3-(1,2,4,5-tetrahydro-benzo[d]azepin-3-yl)-pyrazine-2-carbonitrile | 12 | 0.006 |
| 5-ethyl-6-methyl-3-(1,2,4,5-tetrahydro-benzo[d]azepin-3-yl)-pyrazine-2-carbonitrile | 12 | 0.103 |
| 3-(1,2,4,5-tetrahydro-benzo[d]azepin-3-yl)-pyrazine-2-carbonitrile | 13 | 0.47 |
| 5-methyl-6-phenyl-3-(1,2,4,5-tetrahydro-benzo[d]azepin-3-yl)-pyrazine-2-carbonitrile | 14 | 0.045 |
| 5-(2-hydroxy-ethylamino)-3-(1,2,4,5-tetrahydro-benzo[d]azepin-3-yl)-pyrazine-2-carbonitrile | 15 | 0.5 |

The compounds of formula I and pharmaceutically acceptable salts thereof can be used as pharmaceutical compositions, e.g. in the form of pharmaceutical preparations. The pharmaceutical preparations can be administered orally, e.g. in the form of tablets, coated tablets, dragees, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical compositions containing a compound of formula I or a pharmaceutically acceptable salt thereof and a therapeutically inert excipient are also an object of the present invention, as is a process for the production of such pharmaceutical compositions which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of pharmaceutical compositions, especially for the control or prevention of acute and/or chronic neurological disorders of the aforementioned kind, is also an object of the invention.

The following examples are provided for illustration of the invention. They should not be considered as limiting the scope of the invention, but merely as being representative thereof.

EXAMPLE 1

3-(2-Methoxy-ethoxy)-5-(1,2,4,5-tetrahydro-benzo[d]azepin-3-yl)-[1,2,4]triazine-6-carbonitrile a) 5-Chloro-3-methylsulfanyl-[1,2,4]triazine-6-carbonitrile A solution of 500 mg (2.7 mmol) of 3-methylsulfanyl-5-oxo-4,5-dihydro-[1,2,4]triazine-6-carboxylic acid amide (J. J. Huang, J. Org. Chem. 1985, 50, 2293–2298; H. Wang et al., Hua Hsueh Hsueh Pao 1964, 30(2), 183–192; CA Vol. 61, 8311b) in 38 ml (408 mmol) of phosphorus oxychloride was heated to reflux during 1.5 h. After cooling of the dark brown reaction mixture, the excess of phosphorus oxychloride was evaporated under reduced pressure. To destroy residues of phosphorus oxychloride and to neutralize the reaction mixture, the resulting red-brown oily residue was dissolved in 15 ml of toluene and the solution added to an ice-cold saturated aqueous solution of sodium hydrogencarbonate. The organic phase was diluted with 100 ml of dichloromethane, separated from the aqueous phase, dried over sodium sulfate, and evaporated under reduced pressure. The resulting 5-chloro-3-methylsulfanyl-[1,2,4]triazine-6-carbonitrile was obtained as a brown oil and was used in the following reactions without further purification.

b) 3-Methylsulfanyl-5-(1,2,4,5-tetrahydro-benzo[d]azepin-3-yl)-[1,2,4]triazine-6-carbonitrile A solution of 395 mg (2.7 mmol) of 2,3,4,5-tetrahydro-1H-3-benzazepine hydrochloride [J. Heterocycl. Chem. 1971, 8(5), 779–83] in 5 ml of ethanol was treated at room temperature with 0.92 ml (5.4 mmol) of Huenig's base and, thereupon, with a solution of 501 mg (2.7 mmol) of crude 5-chloro-3-methylsulfanyl-[1,2,4]triazine-6-carbonitrile in 5 ml of ethanol. The dark brown reaction mixture was stirred during 18 h at room temperature. For the working-up, the product, partially precipitated in pure form, was filtered and the resulting mother liquor evaporated under reduced pressure. The residue was chromatographed on silica gel with a 2:1 v/v mixture of hexane and ethylacetate as the eluent. In total, 470 mg (58.5% of theory) of 3-methylsulfanyl-5-(1,2,4,5-tetrahydro-benzo[d]azepin-3-yl)-[1,2,4]triazine-6-carbonitrile were obtained in the form of a beige powder; MS: 298 (M+H)$^+$.

c) 3-(2-Methoxy-ethoxy)-5-(1,2,4,5-tetrahydro-benzo[d]azepin-3-yl)-[1,2,4]triazine-6-carbonitrile Under an argon atmosphere at 0° C., a solution of 25.6 mg (0.34 mmol) of 2-methoxy-ethanol in 2 ml of tetrahydrofurane was treated with 15 mg (0.34 mmol) of sodium hydride (55% dispersion in refined oil) and stirred during 15 min. To this mixture, a solution of 100 mg (0.34 mmol) of 3-methylsulfanyl-5-(1,2,4,5-tetrahydro-benzo[d]azepin-3-yl)-[1,2,4]triazine-6-carbonitrile in 3 ml of tetrahydrofurane was added and stirring continued for 18 h at 40° C. The yellow solution was evaporated under reduced pressure and the residue (141 mg) was chromatographed on silica gel with a 99:1 v/v mixture of dichloromethane and methanol as eluent. Thus were obtained 10 mg (9% of theory) of 3-(2-methoxy-ethoxy)-5-(1,2,4,5-tetrahydro-benzo[d]azepin-3-yl)-[1,2,4]triazine-6-carbonitrile as a light yellow solid; MS: 326 (M+H)$^+$.

EXAMPLE 2

3-Amino-5-(1,2,4,5-tetrahydro-benzo[d]azepin-3-yl)-[1,2,4]triazine-6-carbonitrile A dispersion of 200 mg (0.67 mmol) of 3-methylsulfanyl-5-(1,2,4,5-tetrahydro-benzo[d]azepin-3-yl)-[1,2,4]triazine-6-carbonitrile, which was obtained according to the method as described in example 1b, and 1.0 ml of ammonium hydroxide (1.34 M) was heated under stirring in a sealed tube at 140° C. overnight. To complete the reaction, another 1.0 ml of ammonium hydroxide (1.34 M) was added. Heating was continued under the aforementioned conditions for 18 h. The limpid solution was evaporated under reduced pressure and the residue was chromatographed on silica gel with a 95:5 v/v mixture of dichloromethane and methanol as the eluent. There were obtained 40 mg (22% of theory) of 3-amino-5-(1,2,4,5-tetrahydro-benzo[d]azepin-3-yl)-[1,2,4]triazine-6-carbonitrile as a light yellow solid; MS: 267 (M+H)$^+$.

EXAMPLE 3

3-Dimethylamino-5-(1,2,4,5-tetrahydro-benzo[d]azepin-3-yl)-[1,2,4]triazine-6-carbonitrile In an analogous manner as described in example 2, reaction of 3-methylsulfanyl-5-(1,2,4,5-tetrahydro-benzo[d]azepin-3-yl)-[1,2,4]triazine-6-carbonitrile with dimethylamine (33% solution in absolute ethanol) in a sealed tube at 110° C. yielded 3-dimethylamino-5-(1,2,4,5-tetrahydro-benzo[d]azepin-3-yl)-[1,2,4]triazine-6-carbonitrile as a light brown amorphous solid; MS: 295 (M+H)$^+$.

EXAMPLE 4

3-(Cyclopropylmethyl-amino)-5-(1,2,4,5-tetrahydro-benzo[d]azepin-3-yl)-[1,2,4]triazine-6-carbonitrile A mixture of 150 mg (0.50 mmol) of 3-methylsulfanyl-5-(1,2,4,5-tetrahydro-benzo[d]azepin-3-yl)-[1,2,4]triazine-6-carbonitrile as prepared in example 1b and 74 mg (1.0 mmol) of aminomethyl-cyclopropane in 5 ml of dioxane was stirred at 120° C. overnight. The solution was evaporated under reduced pressure and the residue was chromatographed on silica gel with a 98:2 v/v mixture of dichloromethane and methanol as the eluent. There were obtained 57 mg (35% of theory) of 3-(cyclopropylmethyl-amino)-5-(1,2,4,5-tetrahydro-benzo[d]azepin-3-yl)-[1,2,4]triazine-6-carbonitrile as a white solid; MS: 321 (M+H)$^+$.

EXAMPLE 5
3-(2-Hydroxy-ethylamino)-5-(1,2,4,5-tetrahydro-benzo[d]azepin-3-yl)-[1,2,4]triazine-6-carbonitrile In analogy to the procedure as described in example 4 the 3-methylsulfanyl-5-(1,2,4,5-tetrahydro-benzo[d]azepin-3-yl)-[1,2,4]triazine-6-carbonitrile was reacted with ethanolamine in dioxane at 140° C. overnight to give 3-(2-hydroxyethylamino)-5 -(1,2,4,5-tetrahydro-benzo[d]azepin-3-yl)-[1,2,4]triazine-6-carbonitrile as a light yellow solid; MS: 311 (M+H)$^+$.

EXAMPLE 6
(RS)-3-(2-Hydroxy-propylamino)-5-(1,2,4,5-tetrahydro-benzo[d]azepin-3-yl)-[1,2,4]triazine-6-carbonitrile In analogy to the procedure as described in example 4 the 3-methylsulfanyl-5-(1,2,4,5-tetrahydro-benzo[d]azepin-3-yl)-[1,2,4]triazine-6-carbonitrile was reacted with (RS)-1-amino-2-propanol in dioxane at 120° C. overnight to give (RS)-3-(2-hydroxy-propylamino)-5-(1,2,4,5 -tetrahydro-benzo[d]azepin-3-yl)-[1,2,4]triazine-6-carbonitrile as a white solid; MS: 325 (M+H)$^+$.

EXAMPLE 7
3-Hydrazino-5-(1,2,4,5-tetrahydro-benzo[d]azepin-3-yl)-[1,2,4]triazine-6-carbonitrile In analogy to the procedure as described in example 4 the 3-methylsulfanyl-5-(1,2,4,5-tetrahydro-benzo[d]azepin-3-yl)-[1,2,4] triazine-6-carbonitrile was reacted with hydrazine hydrate in dioxane at 140° C. during 3 hours to give 3-hydrazino-5-(1,2,4,5-tetrahydro-benzo[d]azepin-3-yl)-[1,2,4]triazine-6-carbonitrile as a yellow amorphous powder; MS: 282 (M+H)$^+$.

EXAMPLE 8
{2-[6-Cyano-5-(1,2,4,5-tetrahydro-benzo[d]azepin-3-yl)-[1,2,4]triazin-3-ylamino]-ethyl}-Carbamic Acid Tert-Butyl Ester In analogy to the procedure described in example 4 the 3-methylsulfanyl-5-(1,2,4,5-tetrahydro-benzo[d]azepin-3-yl)-[1,2,4]triazine-6-carbonitrile was reacted with (2-aminoethyl)-carbamic acid tert-butyl ester in dioxane at 120° C. overnight to give {2-[6-cyano-5-(1,2,4,5-tetrahydro-benzo[d]azepin-3-yl)-[1,2,4]triazin-3-ylamino]-ethyl}-carbamic acid tert-butyl ester as a white solid; MS: 410 (M+H)$^+$.

EXAMPLE 9
3-(2-Pyridin-3-yl-ethylamino)-5-(1,2,4,5-tetrahydro-benzo[d]azepin-3-yl)-[1,2,4]triazine-6-carbonitrile A solution of 120 mg (0.40 mmol) of 3-methylsulfanyl-5-(1,2,4,5-tetrahydro-benzo[d]azepin-3-yl)-[1,2,4]triazine-6-carbonitrile in 5 ml of dichloromethane was treated at room temperature with 109 mg (0.44 mmol) of 3-chloroperbenzoic acid (70%). After 2 hours the reaction mixture was evaporated under reduced pressure, and, without working-up and characterization, the resulting crude 3-methanesulfonyl-5-(1,2,4,5-tetrahydro-benzo[d]azepin-3-yl)-[1,2,4]triazine-6-carbonitrile was directly treated with a solution of 108 mg (0.88 mmol) of 3-(2-aminoethyl)pyridine in 10 ml of dioxane. The reaction mixture was then stirred at 80° C. overnight. The reaction mixture was then evaporated under reduced pressure and the residue obtained directly chromatographed on silica gel with a 95:5:0.1 v/v/v mixture of dichloromethane, methanol and ammonium hydroxide as the eluent. There were obtained 55 mg (37% of theory) of 3-(2-pyridin-3-yl-ethylamino)-5 -(1,2,4,5-tetrahydro-benzo[d]azepin-3-yl)-[1,2,4]triazine-6-carbonitrile as a white amorphous solid; MS: 372 (M+H)$^+$.

EXAMPLE 10
3-Hydroxy-5-(1,2,4,5-tetrahydro-benzo[d]azepin-3-yl)-[1,2,4]triazine-6-carbonitrile A solution of 200 mg (0.67 mmol) of 3-methylsulfanyl-5-(1,2,4,5-tetrahydro-benzo[d]azepin-3-yl)-[1,2,4]triazine-6-carbonitrile in 10 ml of dichloromethane was cooled to 0° C. and treated with 332 mg (1.35 mmol) of 3-chloroperbenzoic acid (70%). The reaction mixture was warmed up to room temperature and stirred overnight. For the working-up, the reaction mixture was diluted with 10 ml of dichloromethane and extracted twice with 10 ml of a saturated solution of sodium hydrogencarbonate. The combined organic phases were dried over sodium sulfate, and evaporated under reduced pressure. The resulting residue, 170 mg of a yellow powder, was purified by chromatograhy on silica gel with a 98:2 mixture of dichloromethane and methanol as eluent. There were obtained 154 mg (86% of theory) of 3-hydroxy-5-(1,2,4,5-tetrahydro-benzo[d]azepin-3-yl)-[1,2,4]triazine-6-carbonitrile as a yellowish solid; MS: 266 (M−H).

EXAMPLE 11
3-(2-Amino-ethylamino)-5-(1,2,4,5-tetrahydro-benzo[d]azepin-3-yl)-[1,2,4]triazine-6-carbonitrile trifluoro-acetate To a solution of 60 mg (0.15 mmol) of {2-[6-cyano-5-(1,2,4,5-tetrahydro-benzo[d]azepin-3-yl)-[1,2,4]triazin-3-ylamino]-ethyl}-carbamic acid tert-butyl ester as prepared in example 8 in 2 ml of dichloromethane were added 0.2 ml of trifluoroacetic acid. The reaction mixture was stirred at room temperature for one hour and then evaporated under reduced pressure. The solid residue was dispersed in ether. The resulting solid was filtered and gave 30 mg (47% of theory) of 3-(2-amino-ethylamino)-5 -(1,2,4,5-tetrahydro-benzo[d]azepin-3-yl)-[1,2,4]triazine-6-carbonitrile trifluoro-acetate as an off-white solid; MS: 310 (M+H)$^+$.

EXAMPLE 12
12-1) 5-Ethyl-6-methyl-3-(1,2,4,5-tetrahydro-benzo[d]azepin-3-yl)-pyrazine-2-carbonitrile and
12-2) 6-Ethyl-5-methyl-3-(1,2,4,5-tetrahydro-benzo[d]azepin-3-yl)-pyrazine-2-carbonitrile
a) 5-Ethyl-6-methyl-3-oxo-3,4-dihydro-pyrazine-2-carboxylic acid amide and 6-ethyl-5-methyl-3 -oxo-3,4-dihydro-pyrazine-2-carboxylic Acid Amide A solution of 8.32 g (80.61 mmol) 2-amino-malonic acid diamide and 9.75 g (83.26 mmol) of 2,3-pentanedione in 60 ml of water was heated under reflux for 18 hours. After cooling to room temperature the crystals formed were collected by filtration and dried in vacuo. There were thus obtained 9.52 g (52.54 mmol, 65.2% of theory) of a 3:2 or a 2:3 mixture of the 6-ethyl-5-methyl-3-oxo-3,4-dihydro-pyrazine-2-carboxylic acid amide and the 5-ethyl-6-methyl-3-oxo-3,4-dihydro-pyrazine-2-carboxylic acid amide as yellow solid; MS: 181 (M)$^+$.
b) 3-Chloro-6-ethyl-5-methyl-pyrazine-2-carbonitrile and 3-chloro-5-ethyl-6-methyl-pyrazine-2-carbonitrile (1:1 Mixture of the Two Isomers)

1.81 g (10.0 mmol) of the 3:2 or 2:3 mixture of the 6-ethyl-5-methyl-3-oxo-3,4-dihydro-pyrazine-2 -carboxylic acid amide and the 5-ethyl-6-methyl-3-oxo-3,4-dihydro-pyrazine-2 -carboxylic acid amide were suspended in 4.2 ml (30 mmol) of triethylamine. Then, 30 ml of phosphorus oxychloride were slowly added between 0° C. and 5° C. and the reaction mixture heated under reflux for 3 hours. It was then cooled to 20° C., 5.3 g (25 mmol) of phosphorus pentachloride were added and the reaction mixture heated again under reflux for 3 hours. It was then added to water while maintaining a temperature of 20° C. to 25° C. The aqueous phase was subsequently extracted 5 times with 100 ml of ether and the combined ether phases washed with saturated sodium hydrogen carbonate solution, dried over magnesium sulfate and evaporated under reduced pressure. The residue formed was chromatographed on silica gel using a 1:1 v/v mixture of dichloromethane and hexane as eluent giving 1.0 g (5.5 mmol, 55% of theory) of a 1:1 mixture of the 3-chloro-6-ethyl-5-methyl-pyrazine-2-carbonitrile and the 3-chloro-5-ethyl-6-methyl-pyrazine-2-carbonitrile in form of an orange red oil; MS: 181 (M)$^+$.

c) 5-Ethyl-6-methyl-3-(1,2,4,5-tetrahydro-benzo[d]azepin-3-yl)-pyrazine-2-carbonitrile and 6-ethyl-5-methyl-3-(1,2,4,5-tetrahydro-benzo[d]azepin-3-yl)-pyrazine-2-carbonitrile A solution of 0.300 g (1.65 mmol) of the 1:1 mixture of the 3-chloro-6-ethyl-5-methyl-pyrazine-2 -carbonitrile and the 3-chloro-5-ethyl-6-methyl-pyrazine-2-carbonitrile, of 0.395 g (1.30 mmol) of 2,3,4,5-tetrahydro-1H-benzo[d]azepine hydrochloride (J. Heterocycl. Chem. 1971, 8(5), 779–83) and of 0.566 g (2.60 mmol) of N-ethyl-diisopropylamine in 1.0 ml of N,N-dimethylformamide was stirred at room temperature for 60 hours and then at 60° C. for 18 hours. The reaction mixture was subsequently poured into 50 ml of an ice/water mixture and extracted 3 times with 50 ml of ethylacetate. The combined ethylacetate phases were dried over magnesium sulfate and evaporated under reduced pressure. The residue formed was then chromatographed on silica gel using dichloromethane as eluent giving 0.086 g (0.29 mmol, 18% of theory) of the 6-ethyl-5-methyl-3-(1,2,4,5-tetrahydro-benzo[d]azepin-3-yl)-pyrazine-2-carbonitrile as yellowish solid after crystallization from dichlormethane/pentane; MS: 293 (M+H)$^+$; and 0.074 g (0.25 mmol, 15% of theory) of the 5-ethyl-6-methyl-3-(1,2,4,5-tetrahydro-benzo[d]azepin-3-yl)-pyrazine-2-carbonitrile as yellowish solid; MS: 293 (M+H)$^+$.

EXAMPLE 13

3-(1,2,4,5-Tetrahydro-benzo[d]azepin-3-yl)-pyrazine-2-carbonitrile

In analogy to the procedure as described in example 12 the 2-chloro-3-cyanopyrazine (J. Chem. Soc., Perkin Trans. 1 1991, 11, 2877–81) was treated with 2,3,4,5-tetrahydro-1 H-benzo[d]azepine hydrochloride (J. Heterocycl. Chem. 1971, 8(5), 779–83) and N-ethyl-diisopropylamine in N,N-dimethylformamide at room temperature followed by 60° C. to yield the 3-(1,2,4,5-tetrahydro-benzo[d]azepin-3-yl)-pyrazine-2-carbonitrile as light yellow solid; MS: 251 (M+H)$^+$.

EXAMPLE 14

5-Methyl-6-phenyl-3-(1,2,4,5-tetrahydro-benzo[d]azepin-3-yl)-pyrazine-2-carbonitrile In analogy to the procedure described in example 12 1-phenyl-1,2-propanedione and 2-aminomalonamide were heated in an aqueous solution to give 5-methyl-3-oxo-6-phenyl-3,4 -dihydro-pyrazine-2-carboxylic acid amide. Then, the 5-methyl-3-oxo-6-phenyl-3,4-dihydro-pyrazine-2-carboxylic acid amide was treated with triethylamine and phosphorus pentachloride in phosphorus oxychloride at reflux to give the 3-chloro-5-methyl-6-phenyl-pyrazine-2-carbonitrile. The 3-chloro-5-methyl-6-phenyl-pyrazine-2-carbonitrile was finally treated with 2,3,4,5-tetrahydro-1H-benzo[d]azepine hydrochloride (J. Heterocycl. Chem. 1971, 8(5), 779–83) and N-ethyldiisopropylamine in N,N-dimethylformamide at room temperature to yield the 5-methyl-6-phenyl-3-(1,2,4,5-tetrahydro-benzo[d]azepin-3-yl)-pyrazine-2-carbonitrile as yellow amorphous solid; MS: 341 (M+H)$^+$.

EXAMPLE 15

5-(2-Hydroxy-ethylamino)-3-(1,2,4,5-tetrahydro-benzo[d]azepin-3-yl)-pyrazine-2-carbonitrile a) 3-Bromo-5-chloro-pyrazine-2-carbonitrile A solution of 0.309 g (2.00 mmol) of the 3-amino-5-chloro-pyrazine-2-carbonitrile (J. Org. Chem. 1975, 40, 2341–2347) in 5.0 ml of acetonitrile was slowly added at a temperature of 65° C. to a suspension of 0.903 g (4.0 mmol) of copper(II)bromide and 0.344 g (3.0 mmol) of tert.-butyl nitrite in 20.0 ml of acetonitrile. The reaction mixture was stirred at 65° C. for 1 hour, then cooled to room temperature. It was subsequently poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 4:1 to 0:10 v/v gradient of hexane and dichloromethane as the eluent giving 0.333 g (1.53 mmol, 76.2% of theory) of the 3-bromo-5-chloro-pyrazine-2-carbonitrile as light yellow amorphous solid; MS: 218 (M)$^+$.

b) 3-Bromo-5-(2-hydroxy-ethylamino)-pyrazine-2-carbonitrile 0.061 g (1.00 mmol) of ethanolamine were added slowly at room temperature to a solution of 0.218 g (1.0 mmol) of the 3-bromo-5-chloro-pyrazine-2-carbonitrile and 0.264 g (2.0 mmol) of N-ethyldiisopropylamine in 15.0 ml of dioxane. The reaction mixture was stirred at room temperature for 18 hours. It was subsequently poured into 50 ml of an ice/water/sodium hydrogen carbonate mixture and extracted 3 times with 50 ml of ethylacetate. The combined ethylacetate phases were dried over magnesium sulfate and evaporated under reduced pressure. The residue formed was chromatographed on silica gel with a 100:0 to 95:5 v/v gradient of dichloromethane and methanol as the eluent giving 0.131 g (0.539 mmol, 53.9% of theory) of the 3-bromo-5-(2-hydroxy-ethylamino)-pyrazine-2-carbonitrile as yellow amorphous solid; MS: 243 (M)$^+$.

c) 5-(2-Hydroxy-ethylamino)-3-(1,2,4,5-tetrahydro-benzo[d]azepin-3-yl)-pyrazine-2-carbonitrile 0.415 g (3.00 mmol) of potassium carbonate were added slowly at room temperature to a solution of 0.243 g (1.0 mmol) of the 3-bromo-5-(2-hydroxy-ethylamino)-pyrazine-2-carbonitrile and 0.220 g (1.2 mmol) of the 2,3,4,5-tetrahydro-1H-benzo[d]azepine hydrochloride (J. Heterocycl. Chem. 1971, 8(5), 779–83) in 10.0 ml of N,N-dimethyl-formamide. The reaction mixture was stirred at room temperature for 64 hours and at 80° C. for 5 hours. It was subsequently poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 9:1 to 0:10 v/v gradient of hexane and ethylacetate as the eluent giving 0.308 g (1.0 mmol, 100% of theory) of the 5-(2-hydroxy-ethylamino)-3-(1,2,4,5-tetrahydro-benzo[d]azepin-3-yl)-pyrazine-2-carbonitrile as light yellow amorphous solid; MS: 310 (M+H)$^+$.

EXAMPLE A

Tablets of the following composition are produced in a conventional manner:

|  | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
| --- | --- |
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of the formula

I wherein $R^1$ is selected from the group consisting of hydrogen, lower alkyl, lower alkenyl, or unsubstituted phenyl or phenyl substituted in meta or para positions with at least one substituent selected from the group consisting of lower alkyl, lower alkoxy or halogen; or is absent, when X is —N= or =N—;

$R^2$ is selected from the group consisting of hydrogen, lower alkyl, lower alkenyl, —O, —S-lower alkyl, —SO$_2$-lower alkyl or —OR, —O(CHR$^a$)$_{m+1}$—OR$^b$, NR$^c_2$, —NH—NR$^d_2$, —N(R$^e$)(CHR$^f$)$_{m+1}$—OR$^g$, —N(R$^h$)(CHR$^i$)$_m$-pyridino, —N(R$^j$)(CHR$^k$)$_n$— (C$_3$–C$_6$)cycloalkyl, —N(R$^l$)(CHR$^m$)$_m$(CR$^n_2$)—NR$^o_2$, or —N(R$^p$)(CHR$^q$)$_{m+1}$—NH—C(O)—O-lower alkyl;

m is 1, 2, 3, 4, 5 or 6;

n is 0, 1, 2, 3, 4 or 5;

R, R$^{a-q}$ are each independently selected from the group consisting of hydrogen, lower alkyl or lower alkenyl;

X is selected from the group consisting of —N=, =N—, >O= or =O<; the dotted line is a bond when R$^2$ is =O, or lower alkenyl, Y is selected from the group consisting of —CH=CH—, —CH=OR$^3$—, —OR$^3$=CH—, CR$^3$=CR$^4$— or S; and $R^3$, $R^4$ are, independently, selected form the group consisting of hydrogen, lower alkyl, lower alkoxy or halogen with the proviso, that when Y represents a vinylene group, only one group $R^3$ and one group $R^4$ may be present in the resultant benzene ring;

or a pharmaceutically acceptable salt thereof in racemic and optically active form.

2. A compound in accordance with claim 1 having the formula

I-A wherein $R^1$ is selected from the group consisting of hydrogen, lower alkyl, lower alkenyl, or unsubstituted phenyl or phenyl substituted in meta or para positions with at least one substituent selected from the group consisting of lower alkyl, lower alkoxy or halogen, or is absent, if X is —N= or =N—;

$R^2$ is selected from the group consisting of hydrogen, lower alkyl, lower alkenyl, =O, —S-lower alkyl, —SO$_2$-lower alkyl or —OR, —O(CHR$^a$)$_{m+1}$—OR$^b$, —NR$^c_2$, —NH—NR$^d_2$, —N(R$^e$)(CHR$^f$)$_{m+1}$—OR$^g$, —N(R$^h$)(CHR$^i$)$_m$-pyridino, —N(R$^j$)(CHR$^k$)$_n$— (C$_3$–C$_6$)cycloalkyl, —N(R$^l$)(CHR$^m$)$_m$(CR$^n_2$)—NR$^o_2$, or —N(R$^p$)(CHR$^q$)$_{m+1}$—NH—C(O)—O-lower alkyl;

m is 1, 2, 3, 4, 5 or 6;

n is 0, 1, 2, 3, 4 or 5;

R, R$^{a-q}$ are independently selected from the group consisting of hydrogen, lower alkyl or lower alkenyl;

X is selected from the group consisting of —N=, =N—, >C= or =C<; the dotted line is a bond in the case when R is =O or lower alkenyl;

or a pharmaceutically acceptable salt thereof in racemic optically active form.

3. A compound of formula I-A in accordance with claim 2, wherein $R^1$ is absent and X is —N= or =N—.

4. A compound of formula I-A in accordance with claim 3, wherein $R^2$ is selected from the group consisting of —$NR^c_2$, —NH—$NR^d_2$, —N($R^e$)(CHR$^f$)$_{m+1}$—OR$^g$, —N($R^h$)(CHR$^i$)$_{m+1}$-pyridino, —N($R^j$)(CHR$^k$)$_n$—($C_3$-$C_6$) cycloalkyl, —N($R^l$)(CHR$^m$)$_m$(CR$^n_2$)—NR$^o_2$, or —N($R^p$) (CHR$^q$)$_{m+1}$—NH—C(O)—O-lower alkyl.

5. A compound of formula I-A in accordance with claim 4 wherein the compound is 3-Amino-5-(1,2,4,5-tetrahydro-benzo[d]azepin-3-yl)-[1,2,4]triazine-6-carbonitrile, 3-hydrazino-5-(1,2,4,5-tetrahydro-benzo[d]azepin-3-yl)-[1,2,4]triazine-6-carbonitrile, or {2-[6-cyano-5-(1,2,4,5-tetrahydro-benzo[d]azepin-3-yl)-[1,2,4]triazin-3-ylamino]-ethyl}-carbamic acid tert-butyl ester.

6. A compound of formula I-A in accordance with claim 3, wherein $R^2$ is selected from the group consisting —N($R^e$) (CHR$^f$)$_{m+1}$—OR$^g$, —N($R^h$)(CHR$^i$)$_m$-pyridino, —N($R^j$) (CHR$^k$)$_n$—($C_3$-$C_6$)cycloalkyl.

7. A compound of formula I-A in accordance with claim 6, wherein the compound is
3-(cyclopropylmethyl-amino)-5-(1,2,4,5-tetrahydro-benzo[d]azepin-3-yl)-[1,2,4]triazine-6-carbonitrile,
3-(2-hydroxy-ethylamino)-5-(1,2,4,5-tetrahydro-benzo[d]azepin-3-yl)-[1,2,4]triazine-6-carbonitrile,
(RS)-3-(2-hydroxy-propylamino)-5 -(1,2,4,5-tetrahydro-benzo[d]azepin-3-yl)-[1,2,4]triazine-6-carbonitrile, or
3-(2-pyridin-3-yl-ethylamino)-5-(1,2,4,5-tetrahydro-benzo[d]azepin-3-yl)-[1,2,4]triazine-6-carbonitrile.

8. A compound of formula I-A in accordance with claim 2, wherein X is >C= or =C<.

9. A compound of formula I-A in accordance with claim 8, wherein $R^1$ and $R^2$ are lower alkyl.

10. A compound of formula I-A in accordance with claim 9, wherein the compound is 5-ethyl-6-methyl-3-(1,2,4,5-tetrahydro-benzo[d]azepin-3-yl)-pyrazine-2-carbonitrile, or 6-ethyl-5-methyl-3-(1,2,4,5-tetrahydro-benzo[d]azepin-3-yl)-pyrazine-2-carbonitrile.

11. A compound of formula I-A in accordance with claim 8, wherein $R^1$ is ethyl.

12. A compound of formula I-A in accordance with claim 8, wherein $R^1$ is selected from the group consisting of unsubstituted phenyl or phenyl substituted in meta or para positions with at least one substituent selected from the group consisting of lower alkyl, lower alkoxy or halogen.

13. A compound of formula I-A in accordance with claim 12, which compound is 5-methyl-6-phenyl-3-(1,2,4,5-tetrahydro-benzo[d]azepin-3-yl)-pyrazine-2-carbonitrile.

14. A compound of formula I-A in accordance with claim 8, wherein $R^2$ is —N($R^e$)(CHR$^f$)$_{m+1}$—OR$^g$ with $R^{efg}$ independently selected from the group consisting of hydrogen, lower alkyl or lower alkenyl.

15. A compound of formula I-A in accordance with claim 14, which compound is 5-(2-hydroxy-ethylamino)-3-(1,2,4,5-tetrahydro-benzo[d]azepin-3-yl)-pyrazine-2-carbonitrile.

16. A compound of formula I according to claim 1 wherein the compound is 3-(2-Methoxy-ethoxy)-5-(1,2,4,5-tetrahydro-benzo[d]azepin-3-yl)-[1,2,4]triazine-6-carbonitrile.

17. A compound of formula I according to claim 1 wherein the compound is 3-Dimethylamino-5-(1,2,4,5-tetrahydro-benzo[d]azepin-3-yl)-[1,2,4]triazine-6-carbonitrile.

18. A compound of formula I according to claim 1 wherein the compound is 3-(1,2,4,5-tetrahydro-benzo[d]azepin-3-yl)-pyrazine-2-carbonitrile.

19. A method of treating pain in a person in need of such treatment comprising administering a therapeutically effective amount of a compound of formula I in accordance with claim 1 or a pharmaceutically acceptable salt thereof in a racemic or optically active form to the person.

20. A method of treating migraine in a person in need of such treatment comprising administering a therapeutically effective amount of a compound of formula I in accordance with claim 1 or a pharmaceutically acceptable salt thereof in a racemic or optically active form to the person.

21. A pharmaceutical composition comprising a compound of formula I according to claim 1 or a pharmaceutically acceptable salt thereof in a racemic or optically active form and a pharmaceutically inert carrier.

22. A process for the manufacture of compounds of formula I in accordance with claim 1 or a pharmaceutically acceptable salt thereof, which process comprises
a) reacting a compound of the formula

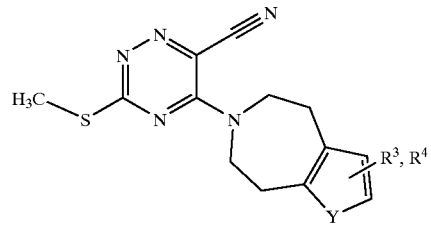

I-2 with a nucleophile including $R^{21}$ to obtain a compound of formula

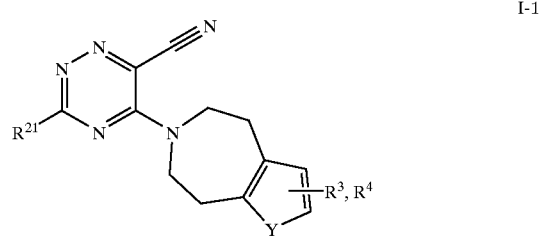

I-1 wherein
$R^{21}$ is selected from the group consisting of —OR, —O(CHR$^a$)$_{m+1}$—OR$^b$, NR$^c_2$, —NH—NR$^d_2$, —N($R^e$)(CHR$^f$)$_{m+1}$—OR$^g$, —N($R^h$)(CHR$^i$)$_m$-pyridino, —N($R^j$)(CHR$^k$)$_n$—($C_3$-$C_6$)cycloalkyl, —N($R^l$)(CHR$^m$)$_m$(CR$^n_2$)—NR$^o_2$, or —N($R^p$) (CHR$^q$)$_{m+1}$—NH—C(O)—O-lower alkyl-;
m is 1, 2, 3, 4, 5 or 6;
n is 0, 1, 2, 3, 4 or 5;
R, $R^{a-q}$ are independently selected from the group consisting of hydrogen, lower alkyl or lower alkenyl;
Y is selected from the group consisting of —CH=CH—, —CH=CR$^3$—, —CR$^3$=CH—, —CR$^3$=CR$^4$— or S;
$R^3$, $R^4$ are, independently, selected form the group consisting of hydrogen, lower alkyl, lower alkoxy or halogen with the proviso, that when Y represents a vinylene group, only one group $R^3$ and one group $R^4$ may be present in the resultant benzene ring and, converting a functional group of $R^{21}$ in a compound of formula I-1 into another functional group to obtain another compound of formula I-1,
and converting a compound of formula I-1 into a pharmaceutically acceptable salt.

23. A process for the manufacture of compounds of formula I-3 or a pharmaceutically acceptable salt thereof, which process comprises reacting a compound of the formula

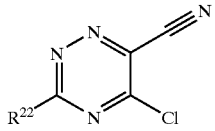

II-1 wherein $R^{22}$ signifies alkyl, with the compound of formula

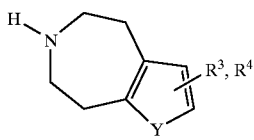

III to obtain a compound of formula

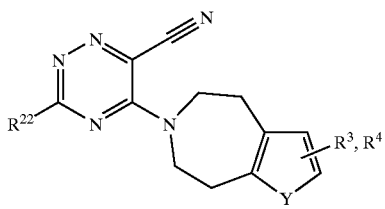

I-3 wherein

Y is selected from the group consisting of —CH=CH—, —CH=CR³—, —CR³=CH—, —CR³=CR⁴— or S;

$R^3$, $R^4$ are, independently, selected form the group consisting of hydrogen, lower alkyl, lower alkoxy or halogen with the proviso, that when Y represents a vinylene group, only one group $R^3$ and one group $R^4$ may be present in the resultant benzene ring and, converting a compound of formula I-3 into a pharmaceutically acceptable salt.

24. A process for the manufacture of compounds of formula I-4 or a pharmaceutically acceptable salt thereof, which process comprises reacting a compound of the formula

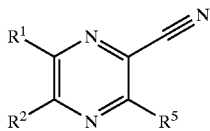

II-2 wherein $R^1$ is selected from the group consisting of hydrogen, lower alkyl, lower alkenyl, or unsubstituted phenyl or phenyl substituted in meta or para positions with at least one substituent selected from the group consisting of lower alkyl, lower alkoxy or halogen, $R^2$ is selected from the group consisting of hydrogen, lower alkyl, lower alkenyl, =O, —S-lower alkyl, —SO-lower alkyl or —OR, —O(CHR$^a$)$_{m+1}$—OR$^b$, —NR$^c_2$, NH—NR$^d_2$, —N(R$^e$)(CHR$^f$)$_m$(CR$^n_2$)NR$^o_2$, or —N(R$^p$)(CHR$^q$)$_{m+1}$—NH—C(O)—O-lower alkyl;

m is 1, 2, 3, 4, 5 or 6;

n is 0, 1, 2, 3, 4 or 5;

R, $R^{a-q}$ are independently selected from the group consisting of hydrogen, lower alkyl or lower alkenyl;

X is selected from the group consisting of —N=, =N—, >C= or =C<; the dotted line is a bond when $R^2$ is =O, or lower alkenyl, Y is selected from the group consisting of —CH=CH—, —CH=CR³—, —CR³=CH—, —CR³=CR⁴— or S; and $R^3$, $R^4$ are, independently, selected form the group consisting of hydrogen, lower alkyl, lower alkoxy or halogen with the proviso, that when Y represents a vinylene group, only one group $R^3$ and one group $R^4$ may be present in the resultant benzene ring;

$R^5$ signifies halogen, with the compound of formula

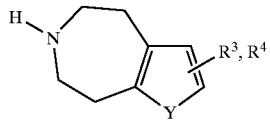

III to obtain a compound of formula

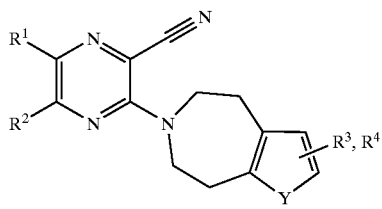

I-4 and converting a compound of formula I-4 into a pharmaceutically acceptable salt.

* * * * *

UNITED STATES PATENT AND TRADEMARK OFFICE
CERTIFICATE OF CORRECTION

PATENT NO. : 6,586,422 B2　　　　　　　　　　　　　　　　　　　　Page 1 of 1
DATED : July 1, 2003
INVENTOR(S) : Binggeli et al.

It is certified that error appears in the above-identified patent and that said Letters Patent is hereby corrected as shown below:

Title page,
Item [75], Inventor, "Alfred Binggeli, Benningen (CH);" should read -- Alfred Binggeli, Binningen (CH); --; and "Wolfgang Wostl, Grenzach-Whylen (DE)" should read -- Wolfgang Wostl, Grenzach-Wyhlen (DE) --.
Item [73], Assignee, "Hoffman-La Roche Inc., Nutley, NJ (US)" should read -- Hoffmann-La Roche Inc., Nutley, NJ (US) --.

Column 22,
Line 8, "-O," should read -- =O, --.
Line 12, "-N($R^i$)(CHR$^k$)$_n$-" should read -- -N($R^j$)(CHR$^k$)$_n$- --.
Line 20, ">O= or =O<;" should read -- >C= or =C<; --.
Line 23, "-CH=OR$^3$-, -OR$^3$=CH-, CR$^3$=CR$^4$- or S;" should read -- -CH=CR$^3$-, -CR$^3$=CH-, -CR$^3$=CR$^4$-or S; --.

Column 26,
Lines 11-13,　　　　　"-SO-lower alkyl or –OR, -O(CHR$^a$)$_{m+1}$-OR$^b$, -NR$^c_2$, NH-NR$^d_2$, -N(R$^e$)(CHR$^f$)$_m$ (CR$^n_2$)NR$^o_2$, or –N(R$^p$)(CHR$^q$)$_{m+1}$-NH-C(O)-

O-lower alkyl;" should read --- -SO$_2$-lower alkyl or –OR, -O(CHR$^a$)$_{m+1}$ –OR$^b$, -NR$^c_2$, -NH-NR$^d_2$,-N(R$^e$)(CHR$^f$)$_{m+1}$ –OR$^g$, -N(R$^h$)(CHR$^i$)$_m$-pyridino, -N(R$^j$)(CHR$^k$)$_n$-

(C$_3$-C$_6$)cycloalkyl, -N(R$^l$)(CHR$^m$)$_m$(CR$^n_2$)-NR$^o_2$, or –N(R$^p$)(CHR$^q$)$_{m+1}$-

NH-C(O)-lower alkyl; --- .

Signed and Sealed this

Eighteenth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,586,422 B2
DATED : July 1, 2003
INVENTOR(S) : Alfred Binggeli et al.

It is certified that error appears in the above-identified patent and that said Letters Patent is hereby corrected as shown below:

Column 22,
Line 65, "R" should read -- $R^2$ --.

Column 26,
Line 27, "form" should read -- from --.

Signed and Sealed this

Twenty-second Day of March, 2005

JON W. DUDAS
*Director of the United States Patent and Trademark Office*